US012734795B2

(12) United States Patent
Fisher et al.

(10) Patent No.: US 12,734,795 B2
(45) Date of Patent: Sep. 15, 2026

(54) METHOD AND APPARATUS FOR PRINTING RADIOPAQUE INDICIA

(71) Applicant: Medical Components, Inc., Harleysville, PA (US)

(72) Inventors: Mark S. Fisher, Sellersville, PA (US); Raymond D. Hawley, East Greenville, PA (US)

(73) Assignee: Medical Components, Inc., Harleysville, PA (US)

( * ) Notice: Subject to any disclaimer, the term of this patent is extended or adjusted under 35 U.S.C. 154(b) by 334 days.

(21) Appl. No.: 18/667,327

(22) Filed: May 17, 2024

(65) Prior Publication Data

US 2024/0336058 A1 Oct. 10, 2024

Related U.S. Application Data

(63) Continuation of application No. 17/181,496, filed on Feb. 22, 2021, now Pat. No. 11,987,042, and a (Continued)

(51) Int. Cl.
*B41F 17/00* (2006.01)
*A61M 39/02* (2006.01)
(Continued)

(52) U.S. Cl.
CPC ....... *B41F 17/001* (2013.01); *A61M 39/0208* (2013.01); *C09D 11/02* (2013.01); (Continued)

(58) Field of Classification Search
CPC ...... A61M 39/0208; A61M 2039/0238; A61M 2207/00
See application file for complete search history.

(56) References Cited

U.S. PATENT DOCUMENTS 4,027,391 A 6/1977 Samis
4,181,132 A 1/1980 Parks
(Continued)

FOREIGN PATENT DOCUMENTS

CN 1901940 A 1/2007
EP 1238682 A2 9/2002
(Continued)

OTHER PUBLICATIONS

"Medical Imprinting Is Too Critical to Do In-House"; CI Medical Imprinting Technology, Inc.; 1 page.
(Continued)

*Primary Examiner* — Dung T Ulsh
(74) *Attorney, Agent, or Firm* — John E. Boyd; FisherBroyles LLP

(57) ABSTRACT

A method of printing radiopaque indicia on a medical device. The method includes applying radiopaque marking fluid to a surface of a plate comprising one or more etchings having a depth of at least 0.0001 inches, exposing the radiopaque marking fluid on the surface of the plate to air to allow the radiopaque marking fluid to achieve a sufficient level of tackiness, and transferring the radiopaque marking fluid to a medical device. The radiopaque marking fluid comprises a clear ink and tungsten particulates having a particulate size of more than one micron.

10 Claims, 5 Drawing Sheets

Related U.S. Application Data continuation of application No. 13/101,878, filed on May 5, 2011, now Pat. No. 10,933,625.

(60) Provisional application No. 61/331,671, filed on May 5, 2010.

(51) Int. Cl.

| | |
|---|---|
| ***B41M 1/10*** | (2006.01) |
| ***B41M 1/22*** | (2006.01) |
| ***B41M 7/00*** | (2006.01) |
| ***C09D 11/02*** | (2014.01) |

(52) U.S. Cl.

CPC ....... *A61M 2039/0238* (2013.01); *B41M 1/10* (2013.01); *B41M 1/22* (2013.01); *B41M 7/00* (2013.01); *B41M 7/009* (2013.01)

(56) References Cited

U.S. PATENT DOCUMENTS

| | | | |
|---|---|---|---|
| 4,560,375 | A | 12/1985 | Schulte |
| 4,673,394 | A | 6/1987 | Fenton, Jr. et al. |
| 4,863,470 | A | 9/1989 | Carter |
| 4,928,298 | A | 5/1990 | Tanaka |
| 5,045,060 | A | 9/1991 | Melsky et al. |
| 5,203,777 | A | 4/1993 | Lee |
| 5,237,922 | A | 8/1993 | Ho |
| 5,322,511 | A | 6/1994 | Armbruster et al. |
| 5,423,334 | A | 6/1995 | Jordan |
| 5,632,205 | A | 5/1997 | Gordon et al. |
| 5,662,600 | A | 9/1997 | Watson et al. |
| 5,806,419 | A | 9/1998 | Adner et al. |
| 6,213,973 | B1 | 4/2001 | Eliasen et al. |
| 6,287,293 | B1 | 9/2001 | Jones et al. |
| 6,314,880 | B1 | 11/2001 | Lampinski |
| 6,356,621 | B1 | 3/2002 | Furumori et al. |
| 6,459,772 | B1 | 10/2002 | Wiedenhoefer et al. |
| 6,527,754 | B1 | 3/2003 | Tallarida et al. |
| 7,785,302 | B2 | 8/2010 | Powers |
| 8,257,325 | B2 | 9/2012 | Schweikert et al. |
| 10,179,230 | B2 | 1/2019 | Powers et al. |
| 2002/0152903 | A1 | 10/2002 | Adner |
| 2004/0019266 | A1 | 1/2004 | Marciante et al. |
| 2004/0068315 | A1 | 4/2004 | Chandrasekaran et al. |
| 2004/0157952 | A1 | 8/2004 | Soffiati |
| 2005/0065434 | A1* | 3/2005 | Bavaro .................. A61B 90/39 600/424 |
| 2007/0233017 | A1* | 10/2007 | Zinn ................. A61M 39/0208 604/288.01 |
| 2007/0270770 | A1 | 11/2007 | Bizup |
| 2007/0272098 | A1 | 11/2007 | Lutz |
| 2008/0131593 | A1 | 6/2008 | Powell |
| 2008/0319399 | A1 | 12/2008 | Schweikert et al. |
| 2009/0264990 | A1 | 10/2009 | Bruszewski et al. |
| 2010/0096596 | A1 | 4/2010 | Lewis |
| 2019/0252603 | A1 | 8/2019 | Wiley et al. |
| 2019/0275311 | A1 | 9/2019 | Hibdon et al. |

FOREIGN PATENT DOCUMENTS

| | | | |
|---|---|---|---|
| EP | 1896117 | B1 | 1/2011 |
| JP | H0199283 | A | 4/1989 |
| JP | H0284349 | A | 3/1990 |
| JP | 2006500087 | A | 1/2006 |
| MX | 2008014737 | A | 12/2008 |
| WO | WO2004004800 | A2 | 1/2004 |

OTHER PUBLICATIONS

"Radiopaque Imprinting Enables Alternative to Angioplasty"; Medical Product Manufacturing News; Apr. 2003; 1 page.

"Radiopaque Ink on Implantable Medical Devices Provides X-Ray Vision to Surgeons"; CI Medical, Inc.; Sep. 27, 2010; 2 pages.

Bill of Materials; 4.8F Low Profile Port Base Annealed—Purple; Radipaque Ink—Black; 1 page.

Extended European Search Report for European Application No. EP 17187448.0 dated Dec. 18, 2017, 10 pages.

Bill of Materials; M-Port Base—Purple; Radipaque Ink—Black; 1 page.

Carlson et al., "Safety Considerations in the Power Injection of Contrast Media via Central Venous Catheters During Computed Tomographic Examinations", Investigative Radiology, vol. 27, No. 5, May 1992, pp. 337-340.

Certificate of Compliance; Purchase Order No. P29319; dated Nov. 21, 2006; 1 page.

Certificate of Compliance; Purchase Order No. P34331-00; dated Jun. 17, 2008; 1 page.

CI Medical Imprinting Technology, Inc.; Radiopaque Ink—Developed for medical/diagnostic applications; 2 pages.

Correspondence from T. Schweikert to B. Mahan dated Sep. 22, 2010; re: Press Releases; 1 page.

Coyle et al., "Power Injection of Contrast Media via Peripherally Inserted Central Catheters for CT", The Journal of the Association for Vascular Access (JAVA), vol. 15, No. 8, Aug. 2004, pp. 809-814.

E-mail communication from B. Mahan to R. Bizup dated Jul. 26, 2006, 4:32 p.m.; re: Radiopaque Printing; 2 pages w/attachment.

E-mail communication from C. Linden to B. Mahan dated Sep. 24, 2008, 11:37 a.m.; re: Additional Questions; 1 page.

E-mail communication from C. Linden to B. Mahan dated Sep. 26, 2008, 12:33 p.m.; re: Medcomp 6 6 process; 2 pages.

E-mail communication from D. Kunin to B. Mahan dated Oct. 21, 2008, 2:57 p.m.; re: Question concerning Tungsten; 1 page.

E-mail communication from J. Callow to B. Mahan dated Oct. 16, 2008, 2:09 p.m.; re: Tungsten Leaching; 3 pages.

E-mail communication from L. Weikert to B. Mahan dated Jan. 2, 2008, 9:52 a.m.; re: Radiopaque Ink; 2 pages.

E-mail communication from R. Bizup to B. Mahan dated Jul. 24, 2006, 5:04 p.m.; re: Radiopaque Printing; 2 pages w/attachment.

E-mail communication from R. Bizup to B. Mahan dated May 13, 2009, 11:16 a.m.; re: samples; 1 page.

Guidance for Industry and FDA Staff, Use of Symbols on Labels and in Labeling of In Vitro Diagnostic Devices Intended for Professional Use, Nov. 30, 2004, 12 pages.

Guidance on Medical Device Patient Labeling; Final Guidance for Industry and FDA Reviewers, Apr. 19, 2001, 54 pages.

Herts et al., "Power Injection of Contrast Media Using Central Venous Catheters: Feasibility, Safety and Efficacy", AJR:176(2), Feb. 2001, pp. 447-453.

Herts et al., "Power Injection of Intravenous Contrast Material Through Central Venous Catheters for CT: In Vitro Evaluation", Radiology, vol. 200, No. 3, Sep. 1996, pp. 731-735.

International Application No. PCT/US2011/035424, International Search Report, dated Aug. 17, 2011, 2 pages.

International Application No. PCT/US2011/035424, Written Opinion, dated Aug. 17, 2011, 4 pages.

IsoMed Constant-Flow Infusion System (Year: 2000), 111 pages.

Purchase Order No. P29319-00; Printed M-Port Base; dated Nov. 13, 2006; 1 page.

Purchase Order No. P34331-00; Re: Printed 4.8F Low Profile Port Base; dated Jun. 9, 2008; 1 page.

Reminders from FDA Regarding Ruptured Vascular Access Devices from Power Injection, Jul. 2004, 2 pages.

Salis et al., "Maximal Flow Rates Possible during Power Injection through Currently Available PICCs: An In-Vitro Study", Journal of the Association for Vascular Access, vol. 15, No. 3, Mar. 2004, pp. 275-281.

Sawyer, "Do It by Design: An Introduction to Human Factors in Medical Devices", U.S. Department of Health and Human Services, Public Health Service, Food and Drug Administration, Center for Devices and Radiological Health, Dec. 1996, 55 pages.

Signs, Symbols, and Icons: Pre-history to the Computer Age, author: Rosemary Sassoon and Albertine Gaur, first published in 1997, 1997, 3 pages.

(56) References Cited

OTHER PUBLICATIONS

Stevens et al., “A Randomized, Prospective Trial of Conventional Vascular Ports vs. The Vortex “Clear-Flow” Reservoir Port in Adult Oncology Patients”, The Journal of Vascular Access Devices, 2000, pp. 37-40.
U.S. Appl. No. 60/658,518, filed Mar. 4, 2005, 78 pages.
U.S. Appl. No. 60/675,309, filed Apr. 27, 2005, 100 pages.
Work Order Cover Sheet; Purchase Order No. P29319; dated Nov. 16, 2006; 1 page.
Work Order Cover Sheet; Purchase Order No. P34331-00; dated Jun. 11, 2008; 1 page.
Written Opinion received for PCT Patent Application No. PCT/US2011/035424, dated Aug. 17, 2011, 4 pages.

* cited by examiner 150
160
140
130
144
142
141
143
120
210
300
350
115
200
110
100

100
110
115
120
130
140
141
142
143
144
150
160
200
210
220
230
300
350

510
570
560
520
550
540
530
500

530
520
510
570
560
550
540
500

400
420
460
410
440
430
450

METHOD AND APPARATUS FOR PRINTING RADIOPAQUE INDICIA

CROSS-REFERENCE TO RELATED APPLICATIONS

This application is a continuation of application Ser. No. 17/181,496, filed Feb. 22, 2021, which is a continuation of application Ser. No. 13/101,878 filed May 5, 2011, which claims the benefit of U.S. provisional application Ser. No. 61/331,671, filed May 5, 2010. The disclosures of which are hereby incorporated by reference in their entirety.

FIELD OF THE INVENTION

This invention relates to a method and apparatus for printing radiopaque indicia on a medical device and, more specifically, to a method and apparatus for printing radiopaque marking fluid onto a venous access port.

BACKGROUND

Venous access ports for the infusion and/or withdrawal of fluids from a patient are known in the art. Such ports generally comprise a needle-penetrable septum, a cap, and a port housing comprising a fluid reservoir. The needle-penetrable septum is disposed on the port housing to seal the fluid reservoir. The cap secures the septum to the port housing. Such ports additionally include a discharge port comprising a fluid passageway that communicates with the fluid reservoir and a catheter secured to the discharge port.

It is desired to provide a venous access port assembly that provides a medical practitioner with capability to discern an important property of the port assembly after the port assembly has been implanted into a patient.

SUMMARY OF THE INVENTION

In accordance with an exemplary aspect of the present invention, there is provided a method of printing radiopaque indicia on a medical device. The method includes applying radiopaque marking fluid to a surface of a plate comprising one or more etchings having a depth of at least 0.0001 inches, exposing the radiopaque marking fluid on the surface of the plate to air to allow the radiopaque marking fluid to achieve a sufficient level of tackiness, and transferring the radiopaque marking fluid to a medical device. The radiopaque marking fluid comprises a clear ink and tungsten particulates having a particulate size of more than one micron.

In accordance with a further exemplary aspect of the present invention, there is provided a printing apparatus for printing radiopaque indicia on a medical device. The printing apparatus includes a plate comprising one or more etchings having a depth of at least 0.0001 inches, a cup containing a radiopaque marking fluid, a jig for holding a medical device, and a pad for transferring radiopaque marking fluid deposited within the one or more etchings to the medical device. The radiopaque marking fluid comprises a clear ink and tungsten particulates having a particulate size of more than one micron. The cup is configured to be inverted and pressed against the plate to effect a fluid seal of the radiopaque marking fluid against the plate.

BRIEF DESCRIPTION OF THE DRAWINGS

For the purpose of illustration, there are shown in the drawings certain exemplary embodiments of the present invention. In the drawings, like numerals indicate like elements throughout. It should be understood, however, that the invention is not limited to the precise arrangements, dimensions, and instruments shown. In the drawings are included the following figures.

DETAILED DESCRIPTION

Figure 1A:
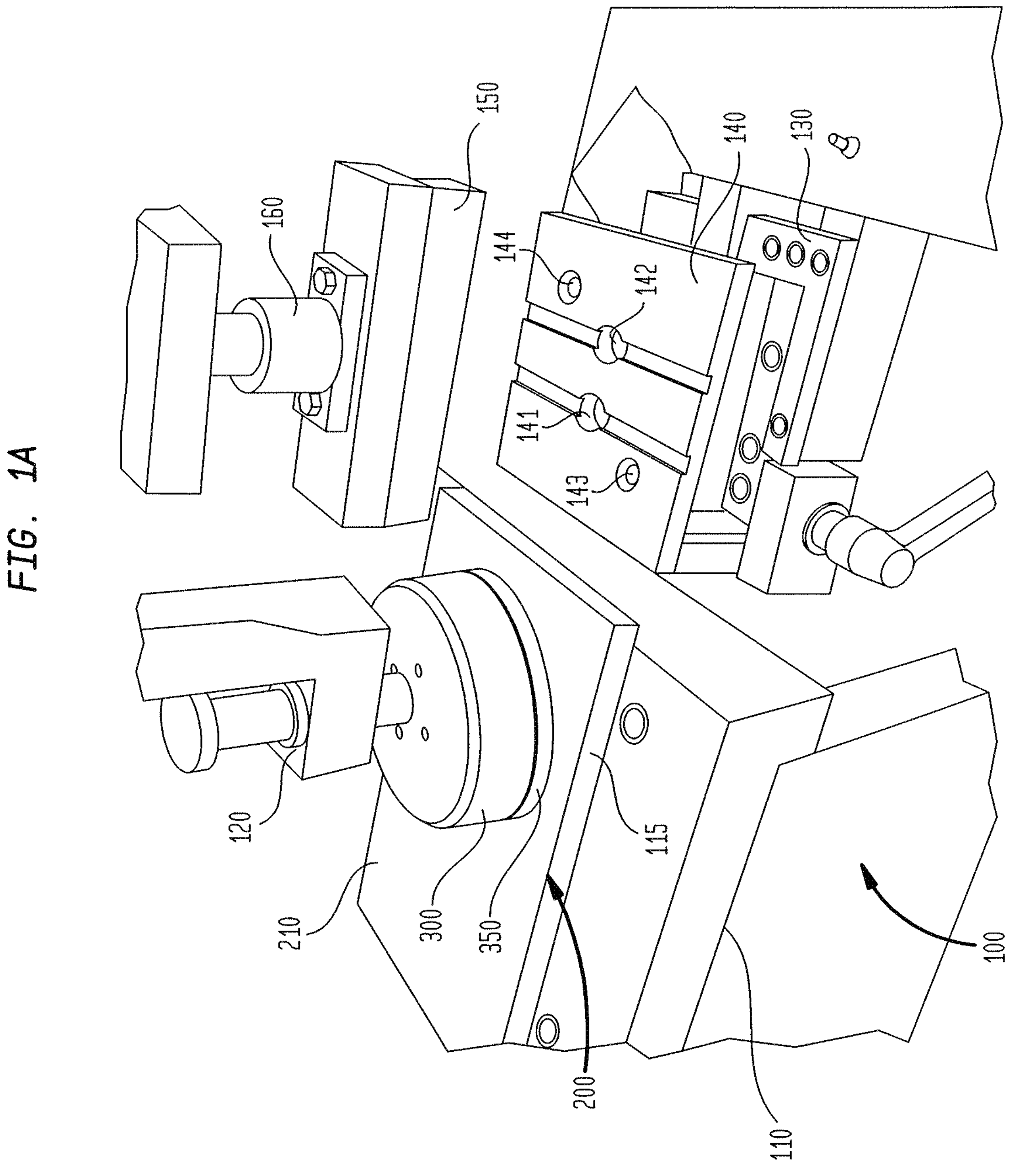
FIG. 1A illustrates an exemplary printing apparatus comprising a cup, a plate, and a pad, wherein the printing apparatus in an idle state (first position) in which the cup is disposed over etchings in the plate, in accordance with an exemplary embodiment of the present invention.

Referring now to FIG. 1A, there is illustrated an exemplary printing apparatus, generally designated as 100, in accordance with an exemplary embodiment of the present invention. The printing apparatus 100 comprises a bed 110 for supporting a plate 200 and a bed 130 for supporting a jig 140 that holds a medical device (not illustrated in FIG. 1A) onto which the exemplary printing apparatus 100 prints indicia.

Mounted onto the bed 110 is a metal plate 115 onto which the plate 200 is secured. In an exemplary embodiment, the metal plate 115 is pinned to the bed 110, and the plate 200 is held in place with dowel pins on the metal plate 115.

The jig 140 includes bolt holes 143 and 144 through which bolts secure the jig 140 to the bed 130. The jig 140 also includes recess 141 and 142 into which medical devices are disposed. The recesses 141 and 142 hold the medical devices in place while the printing apparatus 100 prints indicia onto the medical devices. In an exemplary embodiment, a venous access port assembly is disposed into each of the recesses 141 and 142, with a bottom surface of each access port assembly facing upwards away from the top face of the jig 140.

The printing apparatus 100 additionally comprises a cup 300 attached to an arm 120. Attached to the bottom of the cup 300 is a ring 350. The cup 300 contains ink that is applied to a top surface 210 of the plate 200. The printing apparatus 100 also comprises a pad 150 for transferring the ink on the top surface 210 of the plate 200 to the medical devices in the jig 140.

Figure 1B:
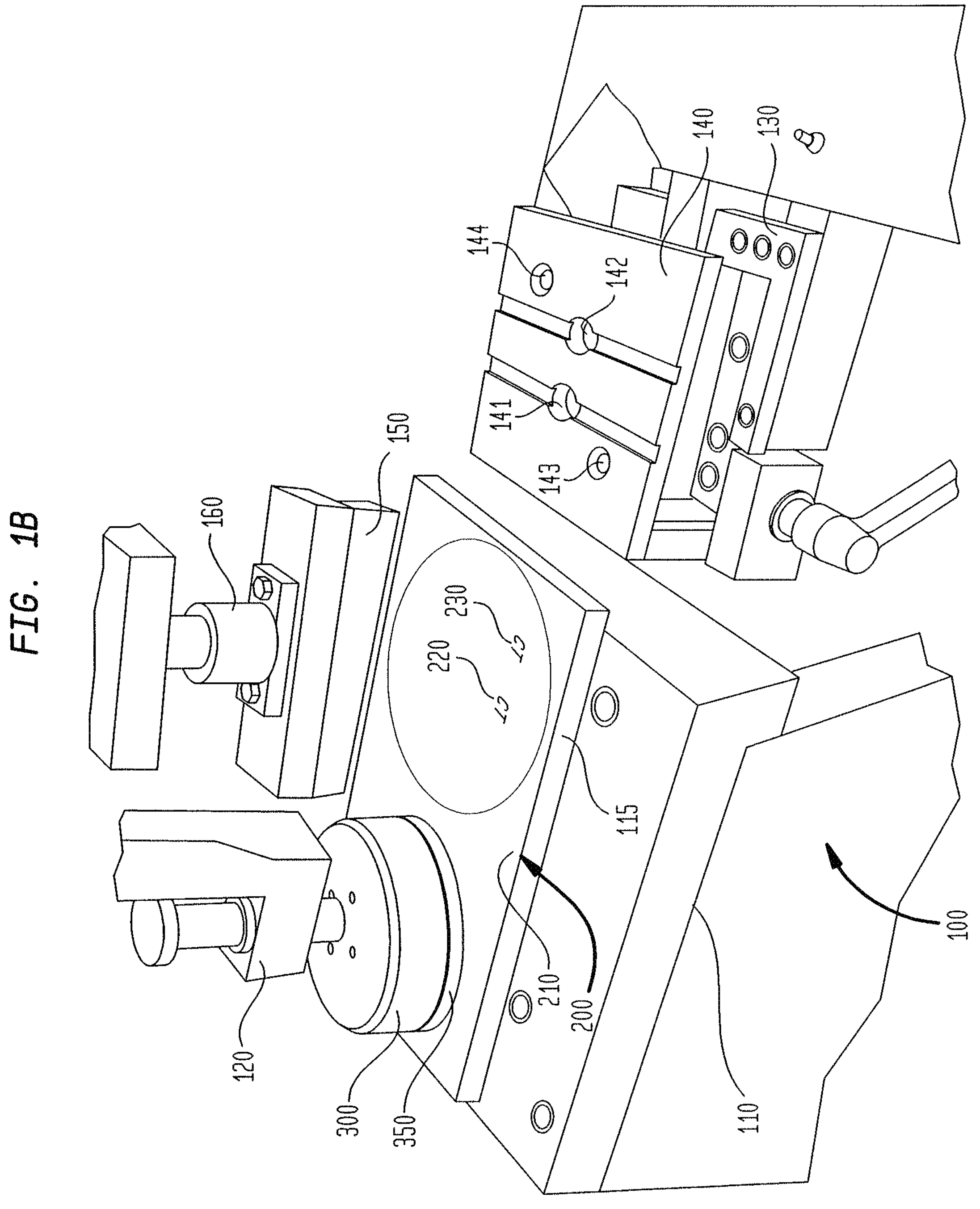
FIG. 1B illustrates the exemplary printing apparatus in a second position in which the cup has been translated off the etchings in the plate, in accordance with an exemplary embodiment of the present invention.

FIG. 1A illustrates an idle state of the printing apparatus 100 in which the cup 300 is in a first position atop the plate 200. Referring now to FIG. 1B, there is illustrated a second position of the cup 300, in accordance with an exemplary embodiment of the present invention. As is illustrated in FIG. 1B, in the second position, the cup 300 is disposed at an end of the plate 200 away from the jig 140. In the second position of the cup 300, etchings 220 and 230 on the top surface 210 of the plate 200 are exposed.

Figure 2:
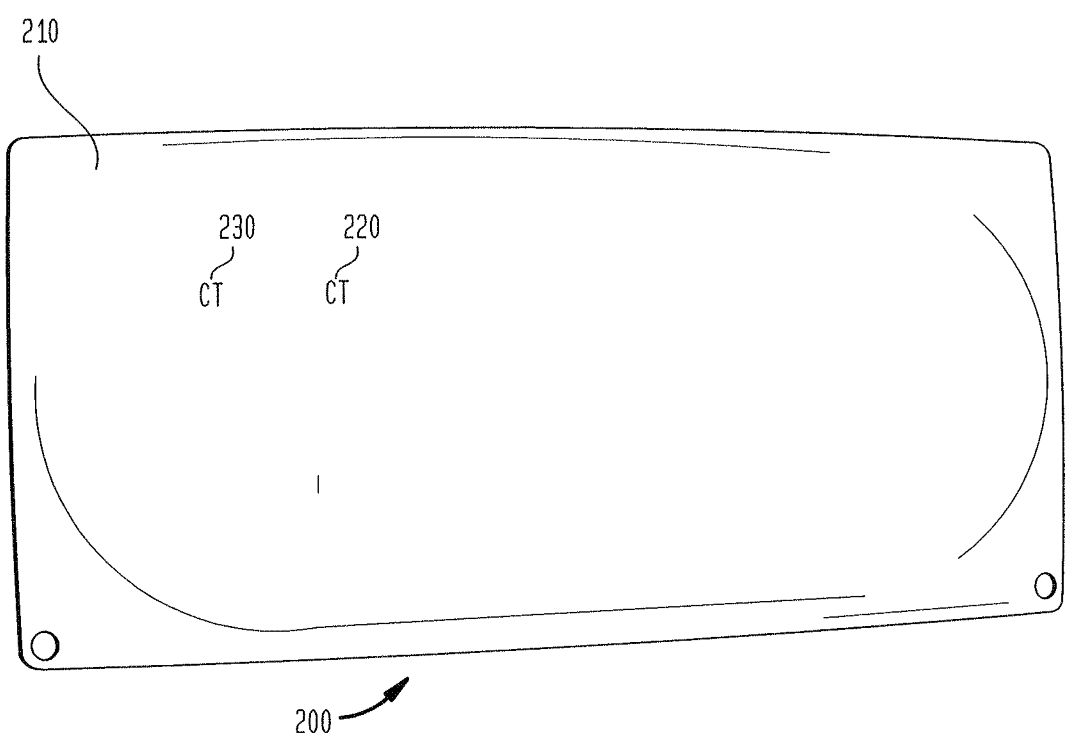
FIG. 2 illustrates the plate of the exemplary printing apparatus, in accordance with an exemplary embodiment of the present invention.

Referring now to FIG. 2, there is illustrated a closer view of the top surface 210 of the plate 200, in accordance with an exemplary embodiment of the present invention. As can be seen in FIG. 2, the etchings 220 and 230 in the top surface 210 of the plate 200 comprise the letters "CT." The exemplary plate 200 is used to print "CT" onto the medical devices, e.g., venous access port assemblies, held by the jig 140.

In an exemplary embodiment, the exemplary printing apparatus 100 prints a radiopaque marking fluid onto the medical devices held in the jig 140. An exemplary radiopaque marking fluid comprises a mixture of a clear ink and tungsten particulates in a defined ratio. Generally, the ratio depends upon the substrate, i.e., the material of the medical devices in the jig 140, on which the radiopaque marking fluid is to be applied. Thus, the ratio depends on the substrate material, the durometer of the substrate, the chemical makeup (compound) of the substrate or the material (substrate) receiving the indicia, and/or processing of the material receiving the indicia. In an exemplary embodiment, the ratio of the mixture is suitable for application to a polysulfone substrate, such as a venous access port assembly formed from polysulfone. Flexible substrates use a radiopaque marking fluid having a clear ink/tungsten ratio that results in the indicia printed onto the medical devices being flexible also to prevent cracking. Stiff substrates allow a clear ink/tungsten ratio that results in stiff indicia printed onto the medical device.

Each of the etchings 220 and 230 have respective depths to accommodate ink applied by the cup 300. In the embodiment in which the exemplary printing apparatus 100 applies radiopaque marking fluid to a medical device, the depths of the etchings 220 and 230 may be between 0.0001 inch (0.000254 cm) and 0.003 inch (0.00762 cm). The depths depend upon the size of the tungsten particulates in the radiopaque marking fluid. Generally speaking, the depths of the etchings 220 and 230 must be increased to accommodate larger tungsten particulates in the radiopaque marking fluid.

Radiopacity of the radiopaque marking fluid varies inversely with the size of the tungsten particulates in the radiopaque marking fluid. Smaller particulates have a lower radiopacity than larger particulates. Thus, when using a radiopaque marking fluid having relatively smaller tungsten particulates, the exemplary printing apparatus 100 desirably performs more hits (applications of radiopaque marking fluid) on the subject medical device to transfer the shape or letters defined by the etchings 220 and 230 onto the medical device, as compared to a lower number of hits required for a radiopaque marking fluid having relatively larger tungsten particulates. Desirable sizes of the tungsten particulates are on the order of one to several microns. In an exemplary embodiment, the size of the tungsten particulates is from one to five microns.

To ensure proper adhesion of the radiopaque marking fluid to the medical devices within the recesses 141 and 142, the medical devices should be cleaned using a suitable cleaning means. Examples of suitable cleaning means include plasma, solvent, aqueous, etc. The cleaning means are not limited to any one technology.

Other specifications of the printing apparatus 100 include the material forming the pad 150, the time for which the radiopaque marking fluid applied in the etchings 220 and 230 are exposed to air before being transferred by the pad 150 to the medical devices, and flash-off time for the radiopaque marking fluid. The firmness of the pad 150 is selected in order to facilitate the transfer of as much radiopaque marking fluid within the etchings 220 and 230 to the medical devices that will adhere to the devices. In a further exemplary embodiment of the printing apparatus 100, the pad 150 is formed from silicone.

The flash-off time of the radiopaque marking fluid is selected so that the radiopaque marking fluid achieves a desired level of tackiness while it is exposed to air before being transferred to the medical devices. Such exposure to air may include blowing chilled air, heated air, or air at room temperature onto the radiopaque marking fluid within the etchings 220 and 230. The temperature and humidity of the air applied to the radiopaque marking fluid within the etchings 220 and 230 is selected to achieve the desired level of tackiness of the radiopaque marking fluid before being transferred to the medical devices.

Figure 3:
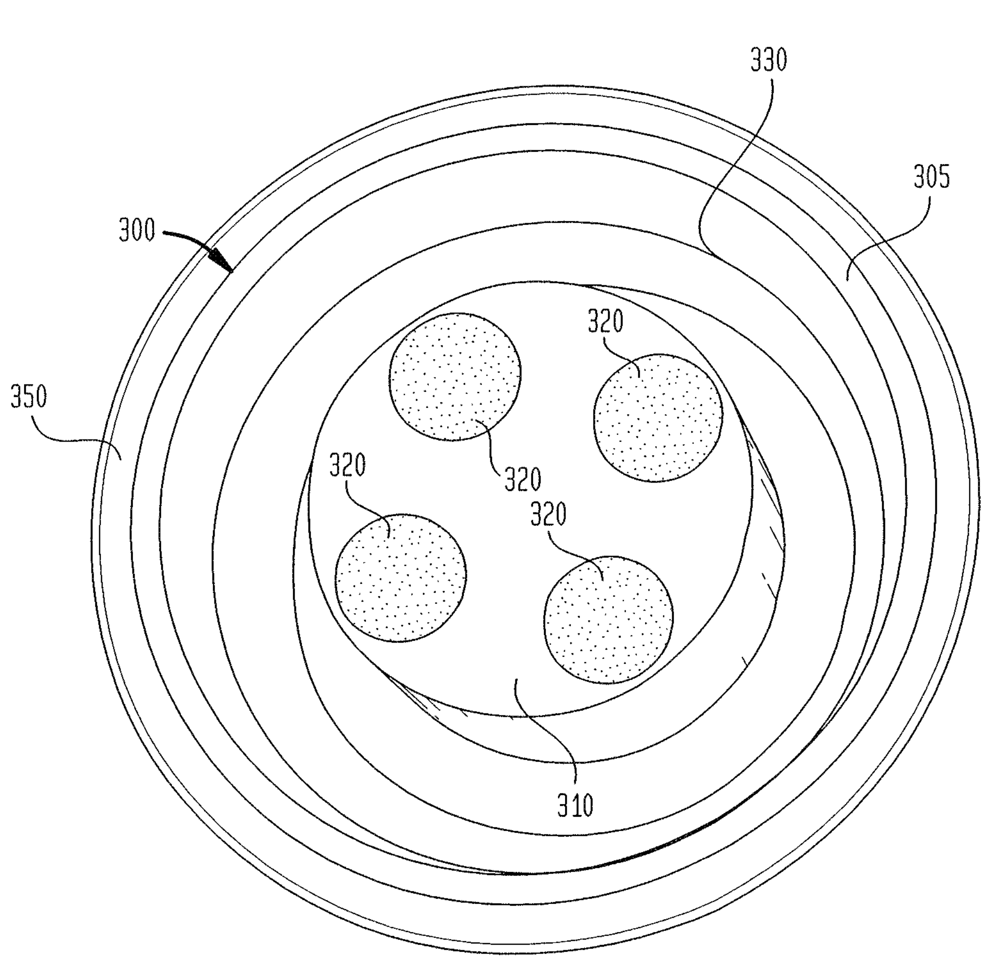
FIG. 3 illustrates the cup of the exemplary printing apparatus, in accordance with an exemplary embodiment of the present invention.

Referring now to FIG. 3, there is illustrated a view of the underside of the cup 300 and the ring 350, in accordance with an exemplary embodiment of the present invention. The cup 300 comprises an outer rim 305 and an inner riser 310. Together, the outer rim 305 and inner riser 310 define an interior cavity 330 which contains the ink or radiopaque marking fluid used in the printing process. The ring 350 is secured to the rim 305 of the cup 300. The ring 350 performs several duties. It seals the ink within the cup 300, specifically within the interior cavity 330 of the cup 300, when the cup 300 is disposed on the plate 200. Further, it acts as a squeegee to wipe ink off the top surface 210 of the plate 200 during the printing process.

Disposed on the riser 310 is a plurality of magnets 320. The magnets 320 are attracted to the plate 200 to allow the ring 350 to perform its sealing and wiping functions. Because the magnets 320 are attracted to the plate 200, the cup 300 compresses the ring 350 against the plate 200 and presses the plate 200 against the metal plate 115.

An exemplary method of printing radiopaque marking fluid onto a bottom surface of venous access port assemblies is now described with reference to FIGS. 1A, 1B, 2, and 3. A technician places venous access port assemblies into the recesses 141 and 142 of the jig 140 and attaches the plate 200 to the metal plate 115. The technician fills the cavity 330 of the cup with a radiopaque marking fluid that will be applied to the venous access port assemblies within the recesses 141 and 142 and subsequent venous access port assemblies that will be placed within the recesses 141 and 142 in subsequent printing operations. The technician then places the printing apparatus 100 in the idle state in which the cup 300 is disposed on the top surface 210 of the plate 200 over the etchings 220 and 230.

In the idle state, the radiopaque marking fluid within the cup 300 covers and fills the etchings 220 and 230 and covers the portion of the top surface 210 over which the cup 300 is disposed. The technician then commands the printing apparatus 100 to transfer the radiopaque marking fluid from the etchings 220 and 230 to the medical devices, i.e., to perform a "hit." The printing apparatus 100 translates the cup 300 away from the etchings 220 and 230. In the process of such translation, the ring 350 secured to the bottom of the cup 300 acts as a squeegee to wipe any radiopaque marking fluid on the top surface 210 of the plate 200 outside of the etchings 220 and 230. The cup 300 moves to the second position, and radiopaque marking fluid remains within the etchings 220 and 230.

The radiopaque marking fluid within the etchings 220 and 230 is then exposed to air to achieve a desired tackiness. Such air may be at room temperature or heated or chilled. When the radiopaque marking fluid achieves the desired level of tackiness, the pad 150 hits the etchings 220 and 230 and picks up some or all of the radiopaque marking fluid within the etchings 220 and 230. The pad 150 then hits the medical devices within the recesses 141 and 142 to transfer the radiopaque marking fluid to the medical devices. The printing apparatus 100 returns to its idle state.

The printing apparatus 100 repeats the process described above to perform additional hits on the medical devices to layer the radiopaque marking fluid on the medical devices to achieve a desired level of radiopacity of the printed indicia. When the desired level of radiopacity is achieved, the medical devices are removed from the jig, and new medical devices are inserted to be printed using the process described above. The deposited radiopaque marking fluid may be allowed to air dry, or the printed medical devices may be placed into an oven to speed the drying process.

Figures 4, 5A, 5B:
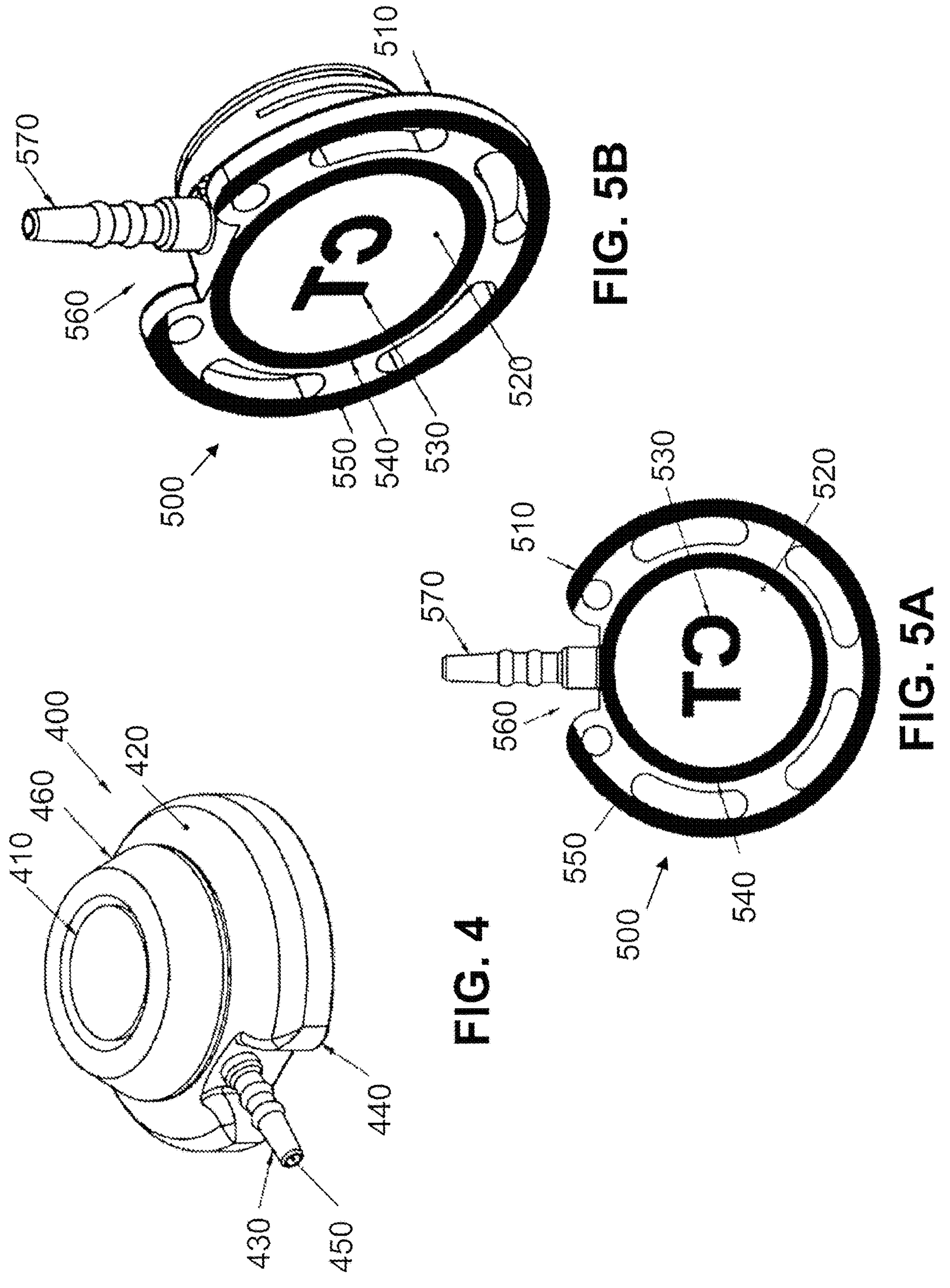
FIG. 4 illustrates an exemplary venous access port assembly, in accordance with an exemplary embodiment of the present invention.
FIG. 5A is a planar view of the bottom of an exemplary venous access port assembly onto which radiopaque indicia have been printed using the exemplary printing apparatus illustrated in FIG. 1, in accordance with an exemplary embodiment of the present invention.
FIG. 5B is an isometric view of the exemplary venous access port assembly of FIG. 5A, in accordance with an exemplary embodiment of the present invention.

Referring now to FIG. 4, there is illustrated an exemplary embodiment of a venous access port assembly, generally designated as 400, in accordance with an exemplary embodiment of the present invention. The venous access port assembly 400 comprises a septum 410 and a housing 420 that includes an interior fluid reservoir (not illustrated). The septum 410 is disposed on the port housing 420 to seal the interior fluid reservoir.

The venous access port assembly 400 additionally comprises a discharge port 430 extending from a distal end 440 of the port assembly 400. The discharge port 430 is attached securely and sealingly to the proximal end of a catheter (not illustrated). A passageway (not illustrated) extends from the interior reservoir to a distal tip opening 450 of discharge port 430. The port assembly further comprises a cap 460 which secures the septum 410 to the port housing 420 to maintain the fluid seal within the interior fluid reservoir.

In an exemplary embodiment of the printing apparatus 100, the recesses 141 and 142 formed within the jig 140 are shaped to hold the access port assembly 400 during the printing process. In such an embodiment, an access port assembly 400 is disposed within each of the recesses 141 and 142 such that the septum 410 of each port assembly 400 faces down and a bottom surface of each port assembly 400 face up toward the pad 150. The printing apparatus 100 applies ink to the bottom surface of each port assembly 400. In an exemplary embodiment, the printing apparatus 100 applies radiopaque marking fluid to the bottom surface of each port assembly 400.

The venous access port assembly 400 is further described in U.S. patent application Ser. No. 11/801,050 filed May 7, 2007 and claiming priority from U.S. Provisional Patent Application Ser. No. 60/801,523 filed May 18, 2006 and in U.S. patent application Ser. No. 12/143,377 filed Jun. 20, 2008 and claiming priority from U.S. Provisional Patent Application Ser. No. 60/936,491 filed Jun. 20, 2007, the contents of all of which applications are hereby incorporated by reference in their entirety for all purposes.

FIG. 5A illustrates a planar view of a port assembly 500 onto which indicia have been printed, in accordance with an exemplary embodiment of the present invention. FIG. 5B illustrates an isometric view of the port assembly 500, in accordance with an exemplary embodiment of the present invention.

Referring now to FIGS. 5A and 5B together, the port assembly 500 comprises a base 510 having a bottom surface 520 onto which indicia have been printed. The indicia include indicia 530 centered on the bottom surface 520 of the port assembly 500. In the example shown, indicia 530 comprise the letters “CT” representing the term “computed tomography.” The meaning of this term is described in further detail below.

The indicia on the bottom surface 520 further include a smaller inner circle 540 and a larger outer circle 550 provided on the outermost periphery of bottom surface 520. The outer circle 550 includes a gap 560 where the port assembly 500 includes a recess to accommodate a stem 570.

In an exemplary embodiment of the printing apparatus 100 described above, the printing apparatus 100 applies radiopaque marking fluid to print radiopaque indicia onto the medical devices disposed within the recesses 141 and 142 of the jig. In such embodiment, the medical devices may be formed from radiotransparent material. In a further exemplary embodiment, the printing apparatus 100 prints radiopaque indicia on venous access port assemblies, such as the port assemblies 400 or 500. In such embodiment, the port assemblies 400 and 500 are formed from a plastic material, such as a silicone elastomer or polysulfone. Thus, in an exemplary embodiment, the indicia 530, the inner circle 540, and the outer circle 550 are printed with radiopaque marking fluid.

A wide variety of medical procedures require infusion of a fluid into a patient. For example, vascular imaging technologies may require use of a contrast media that is injected into the patient. More specifically, computed tomography (CT) is an imaging technology that utilizes a contrast media and may be employed for the noninvasive evaluation and assessment of a vascular system (i.e., CT angiography or CTA). Multidetector computed tomography (MDCT) is one specific type of CT that may be utilized for CTA. For proper imaging of a vascular system via CT, intravenous contrast media injection protocols are coordinated and selected for the anatomic area of interest.

More particularly, conventionally, a so-called “power injector” system may be employed for injecting contrast media at a high pressure into a peripherally inserted intravenous (IV) line. Because CT procedures are often defined in terms of a desired flow rate of contrast media, such power injection systems are, in general, controllable by selecting a desired flow rate. Accordingly, such power injection systems may develop pressure (within the maximum pressure capability of the power injection system) as is necessary to maintain the selected flow rate.

The pressure required for contrast injection depends on many factors, including flow rate, contrast viscosity, configuration of infusion tubing, such as tube diameter and length, and any obstruction or restriction to flow (e.g., kinks, curves, fittings, compression). As mentioned above, to maintain the flow rate required for a CT or MRI study, a power injector may generate high pressures. Ruptures can occur when the injection pressure exceeds the tolerance of the vascular access devices, such as venous access ports. Other problems may occur due to timing errors between the scan and the contrast. In order to maximize the rapid scanning capacity of the newer vascular imaging devices, the starting of the scanning process can be delayed a predetermined amount of time after injection of the contrast media has begun. If the scan starts too early, just as the contrast is arriving at the heart, arteries can appear smaller than they really are when the image is post-processed. On the other hand, if scanning is delayed too long, image artifacts can arise from diluted contrast in the cardiac veins. The window of opportunity for optimal scans may be very small, because contrast media circulates quickly through cardiac arteries and into cardiac veins.

The term "high pressure injection" is understood to mean injections in which pressures within the port assembly 400 or 500 reach pressures generated by power injections having fluid flow rates between about 1 milliliter per second and about 5 milliliters per second. Such pressures may be between about 37 psi (255 kPa) to about 65 psi (448 kPa) within the reservoir of such port assemblies.

Thus, in an exemplary embodiment, the radiopaque indicia, such as the indicia 530, 540, and 550, indicate that the medical device, e.g., the port assembly 500, on which such indicia are printed by the printing apparatus 100, is rated for high pressure injection such as is necessary for infusion into a patient of contrast medium that is used in computed tomography. Hence, in an exemplary embodiment, the indicia 530 comprise the letters "CT." Other indicia may be used that indicate some other attribute or characteristic of the venous access port assembly.

By printing radiopaque indicia onto a venous access port assembly rated for high pressure injections, a clinician is able to verify that such venous access port assembly is rated for high pressure injections after being implanted into a patient. Specifically, such clinician may X-ray the implanted port assembly and be able to verify that such port assembly is rated for high pressure injection if "CT" is discernable on the port assembly in the X-ray image. Further, because the radiopaque marking fluid is applied to an exterior surface of the venous access port assembly, the indicia (e.g., "CT") are viewable to the naked eye prior to implantation. Thus, the surgeon implanting the port assembly is able to verify that such port assembly is rated for high pressure injection by visual inspection of the port assembly prior to implantation. In an exemplary embodiment, the CT indicia appear to be black to the naked eye.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed is:

1. A method of manufacturing a venous access port having printed indicia, the venous access port comprising:

a housing that includes an interior fluid reservoir;

a septum; and a discharge port extending from the reservoir;

the method of manufacturing comprising:

(a) positioning the venous access port on a jig, wherein the jig comprises a plate having at least one recess configured to hold the venous access port;

(b) applying radiopaque marking fluid to a surface of a plate comprising one or more etchings having a depth between 0.0001 inches and 0.003 inches, wherein the radiopaque marking fluid comprises a clear ink and tungsten particulates having at least one particulate size more than 1 micron and no more than 5 microns;

(c) depositing the radiopaque marking fluid onto a surface of the plate around the one or more etchings and into the one or more etchings by placing an inverted cup containing the radiopaque marking fluid onto the surface of the plate over the one or more etchings, the inverted cup comprising a ring that is compressed against the plate due to an attraction by a plurality of magnets disposed on a riser of the inverted cup when the inverted cup is placed onto the surface of the plate, the ring being a structure that circumvents a perimeter of the inverted cup and the riser being a member positioned at a central point of the inverted cup, wherein the plurality of magnets comprises at least four magnets positioned concentrically within the ring and located equidistant from each other;

(d) wiping the radiopaque marking fluid deposited onto the surface of the plate around the one or more etchings off the surface of the plate around the one or more etchings by translating the inverted cup so as to cause the ring to slide along the surface of the plate away from the one or more etchings, thereby exposing the radiopaque marking fluid deposited within the one or more etchings to air to allow the radiopaque marking fluid to achieve a sufficient level of tackiness; and (e) picking up some of the radiopaque marking fluid deposited within the one or more etchings using a silicone pad and transferring the picked up radiopaque marking fluid to the venous access port, the silicone pad having a firmness to facilitate transfer of as much of the radiopaque marking fluid deposited within the one or more etchings to the venous access port that will adhere to the venous access port;

wherein the steps of applying, exposing, and transferring are an application of the radiopaque marking fluid, the application being repeated to achieve an amount of the radiopaque marking fluid on the venous access port having at least a predetermined radiopacity.

2. The method of manufacturing of claim 1, wherein the at least one X-ray discernable indicium comprises letters "CT" and the one or more etchings comprise letters "CT".

3. The method of manufacturing of claim 1, wherein exposing the radiopaque marking fluid deposited within the one or more etchings to air to allow the radiopaque marking fluid to achieve a sufficient level of tackiness further comprises blowing chilled air onto the marking fluid.

4. The method of manufacturing of claim 1, wherein exposing the radiopaque marking fluid deposited within the one or more etchings to air to allow the radiopaque marking fluid to achieve a sufficient level of tackiness further comprises blowing heated air onto the marking fluid.

5. The method of manufacturing of claim 1, wherein exposing the radiopaque marking fluid deposited within the one or more etchings to air to allow the radiopaque marking fluid to achieve a sufficient level of tackiness further comprises blowing ambient air onto the marking fluid.

6. The method of manufacturing of claim 1, wherein the ratio of the clear ink and the tungsten particulates is determined according to a durometer, a chemical makeup and the processing of the material of the venous access port on which the radiopaque marking fluid is to be applied.

7. The method of manufacturing of claim 1, wherein a ratio of the clear ink and the tungsten particulates is determined according to a material of the venous access port on which the radiopaque marking fluid is to be applied.

8. The method of manufacturing of claim 1, wherein the transferring of the picked up radiopaque marking fluid to the venous access port comprises transferring of the picked up radiopaque marking fluid to a bottom surface of the housing.

9. The method of manufacturing of claim 8, wherein the method results in the bottom surface of the housing being printed with at least one X-ray discernable indicium.

10. The method of manufacturing of claim 1, wherein the printed radiopaque marking fluid indicates by visual inspection of the printed venous access port prior to being implanted into a patient, and by X-ray examination after being implanted into a patient, that the venous access port is capable of high-pressure injection.

* * * * *